(12) United States Patent
Walch et al.

(10) Patent No.: US 11,304,815 B2
(45) Date of Patent: Apr. 19, 2022

(54) SET OF GLENOID COMPONENTS FOR A SHOULDER PROSTHESIS

(71) Applicant: HOWMEDICA OSTEONICS CORP., Mahwah, NJ (US)

(72) Inventors: Gilles Walch, Lyons (FR); Pascal Boileau, Nice (FR); Christophe Levigne, Caluire (FR); Lucile Ferrand, Montbonnet (FR); Pierric Deransart, Saint Martin d'uriage (FR)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 40 days.

(21) Appl. No.: 16/840,791

(22) Filed: Apr. 6, 2020

(65) Prior Publication Data

US 2020/0229935 A1    Jul. 23, 2020

Related U.S. Application Data

(60) Continuation of application No. 15/145,210, filed on May 3, 2016, now Pat. No. 10,631,993, which is a
(Continued)

(30) Foreign Application Priority Data

Oct. 22, 2010 (FR) ........................................ 1058647

(51) Int. Cl.
*A61F 2/40* (2006.01)
*A61F 2/30* (2006.01)

(52) U.S. Cl.
CPC .. *A61F 2/4081* (2013.01); *A61F 2002/30166* (2013.01); *A61F 2002/30616* (2013.01);
(Continued)

(58) Field of Classification Search
CPC ...................... A61F 2/4081; A61F 2/40; A61F 2002/30616; A61F 2002/30884
See application file for complete search history.

(56) References Cited

U.S. PATENT DOCUMENTS 3,694,820 A    10/1972 Scales et al.
3,815,157 A     6/1974 Skorecki et al.
(Continued)

FOREIGN PATENT DOCUMENTS

CH         426096      12/1966
CH         507704       5/1971
(Continued)

OTHER PUBLICATIONS

"Aequalis-Fracture Shoulder Prosthesis—Surgical Technique," Tornier, Inc., 2002, in 32 pages.
(Continued)

*Primary Examiner* — Christopher D. Prone
(74) *Attorney, Agent, or Firm* — Duane Morris LLP

(57) ABSTRACT

This set comprises glenoid components that each include a body defining, on two of its opposite faces, respectively, a joint surface, intended to cooperate with a humeral head, and a bearing surface bearing against the socket of a shoulder blade. In this set, the glenoid components are provided in several different sizes, respectively defined by the dimensions of the joint surface of their body. At least two glenoid components of which the bearing surfaces respectively have different dimensional geometries are provided so as to allow the surgeon to improve the durability of the mechanical cooperation between the implanted component and the operated socket.

16 Claims, 2 Drawing Sheets

Related U.S. Application Data division of application No. 13/279,070, filed on Oct. 21, 2011, now Pat. No. 9,351,844.

(60) Provisional application No. 61/488,102, filed on May 19, 2011.

(52) U.S. Cl.
CPC .............. *A61F 2002/30808* (2013.01); *A61F 2002/30884* (2013.01); *A61F 2002/30897* (2013.01); *A61F 2002/30902* (2013.01)

(56) References Cited

U.S. PATENT DOCUMENTS

| | | |
|---|---|---|
| 3,842,442 A | 10/1974 | Kolbel |
| 3,864,758 A | 2/1975 | Yakich |
| 3,869,730 A | 3/1975 | Skobel |
| 3,916,451 A | 11/1975 | Buechel et al. |
| 3,978,528 A | 9/1976 | Crep |
| 3,979,778 A | 9/1976 | Stroot |
| 3,992,726 A | 11/1976 | Freeman et al. |
| 4,003,095 A | 1/1977 | Gristina |
| 4,030,143 A | 6/1977 | Elloy et al. |
| 4,040,131 A | 8/1977 | Gristina |
| 4,054,955 A | 10/1977 | Seppo |
| 4,135,517 A | 1/1979 | Reale |
| 4,179,758 A | 12/1979 | Gristina |
| 4,206,517 A | 6/1980 | Pappas et al. |
| 4,261,062 A | 4/1981 | Amstutz et al. |
| 4,550,450 A | 11/1985 | Kinnett |
| 4,693,723 A | 9/1987 | Gabard |
| 4,822,370 A | 4/1989 | Schelhas |
| 4,846,840 A | 7/1989 | Leclercq et al. |
| 4,865,605 A | 9/1989 | Dines et al. |
| 4,865,609 A | 9/1989 | Roche |
| 4,892,549 A | 1/1990 | Figgie, III et al. |
| 4,919,670 A | 4/1990 | Dale et al. |
| 4,957,510 A | 9/1990 | Cremascoli |
| 4,963,155 A | 10/1990 | Lazerri et al. |
| 4,986,833 A | 1/1991 | Worland |
| 5,032,132 A | 7/1991 | Matsen, III et al. |
| 5,080,673 A | 1/1992 | Burkhead et al. |
| 5,080,685 A | 1/1992 | Bolesky et al. |
| 5,127,920 A | 7/1992 | MacArthur |
| 5,135,529 A | 8/1992 | Paxson et al. |
| 5,152,797 A | 10/1992 | Luckman et al. |
| 5,163,961 A | 11/1992 | Harwin |
| 5,171,289 A | 12/1992 | Tornier |
| 5,181,928 A | 1/1993 | Bolesky et al. |
| 5,192,329 A | 3/1993 | Christie et al. |
| 5,201,882 A | 4/1993 | Paxson |
| 5,206,925 A | 4/1993 | Nakazawa et al. |
| 5,222,984 A | 6/1993 | Forte |
| 5,226,915 A | 7/1993 | Bertin |
| 5,261,914 A | 11/1993 | Warren |
| 5,314,479 A | 5/1994 | Rockwood, Jr. et al. |
| 5,314,485 A | 5/1994 | Judet |
| 5,314,487 A | 5/1994 | Schryver et al. |
| 5,326,359 A | 7/1994 | Oudard |
| 5,330,531 A | 7/1994 | Cappana |
| 5,358,526 A | 10/1994 | Tornier |
| 5,383,936 A | 1/1995 | Kubein-Meesenburg et al. |
| 5,405,399 A | 4/1995 | Tornier |
| 5,425,779 A | 6/1995 | Schlosser et al. |
| 5,429,639 A | 7/1995 | Judet |
| 5,443,519 A | 8/1995 | Averill et al. |
| 5,458,650 A | 10/1995 | Garrett et al. |
| 5,462,563 A | 10/1995 | Shearer et al. |
| 5,505,731 A | 4/1996 | Tornier |
| 5,507,817 A | 4/1996 | Craig et al. |
| 5,507,818 A | 4/1996 | McLaughlin |
| 5,507,824 A | 4/1996 | Lennox |
| 5,531,793 A | 7/1996 | Kelman et al. |
| 5,549,682 A | 8/1996 | Roy |
| 5,580,352 A | 12/1996 | Sekel |
| 5,591,168 A | 1/1997 | Judet et al. |
| 5,603,715 A | 2/1997 | Kessler |
| 5,662,651 A | 9/1997 | Tornier et al. |
| 5,676,702 A | 10/1997 | Ratron |
| 5,702,447 A | 12/1997 | Walch et al. |
| 5,702,457 A | 12/1997 | Walch et al. |
| 5,702,478 A | 12/1997 | Tornier |
| 5,702,486 A | 12/1997 | Craig et al. |
| 5,723,018 A | 3/1998 | Cyprien et al. |
| 5,728,161 A | 3/1998 | Camino et al. |
| 5,741,335 A | 4/1998 | Gerber et al. |
| 5,755,807 A | 5/1998 | Anstaett et al. |
| 5,766,256 A | 6/1998 | Oudard et al. |
| 5,800,551 A | 9/1998 | Williamson et al. |
| 5,824,106 A | 10/1998 | Fournol |
| 5,879,395 A | 3/1999 | Tornier et al. |
| 5,879,405 A | 3/1999 | Ries et al. |
| 5,902,340 A | 5/1999 | White et al. |
| 5,910,171 A | 6/1999 | Kummer et al. |
| 5,928,285 A | 7/1999 | Bigliani |
| 5,944,758 A | 8/1999 | Mansat et al. |
| 5,961,555 A | 10/1999 | Huebner |
| 5,984,927 A | 11/1999 | Wenstrom, Jr. et al. |
| 6,015,437 A | 1/2000 | Stossel |
| 6,033,439 A | 3/2000 | Camino et al. |
| 6,045,582 A | 4/2000 | Prybyla |
| 6,045,583 A | 4/2000 | Gross et al. |
| 6,102,953 A | 8/2000 | Huebner |
| 6,129,764 A | 10/2000 | Servidio |
| 6,162,254 A | 12/2000 | Timoteo |
| 6,165,224 A | 12/2000 | Tornier |
| 6,168,629 B1 | 1/2001 | Timoteo |
| 6,171,341 B1 | 1/2001 | Boileau et al. |
| 6,183,519 B1 | 2/2001 | Bonnin et al. |
| 6,197,062 B1 | 3/2001 | Fenlin |
| 6,197,063 B1 | 3/2001 | Dews |
| 6,203,575 B1 | 3/2001 | Farey |
| 6,206,925 B1 | 3/2001 | Tornier |
| 6,228,120 B1 | 5/2001 | Leonard et al. |
| 6,267,767 B1 | 7/2001 | Strobel et al. |
| 6,283,999 B1 | 9/2001 | Rockwood, Jr. |
| 6,299,646 B1 | 10/2001 | Chambat et al. |
| 6,312,467 B1 | 11/2001 | McGee |
| 6,328,758 B1 | 12/2001 | Tornier et al. |
| 6,334,874 B1 | 1/2002 | Tornier et al. |
| 6,358,250 B1 | 3/2002 | Orbay |
| 6,364,910 B1 | 4/2002 | Schultz et al. |
| 6,368,352 B1 | 4/2002 | Camino et al. |
| 6,368,353 B1 | 4/2002 | Arcand |
| 6,379,387 B1 | 4/2002 | Tornier |
| 6,398,812 B1 | 6/2002 | Masini |
| 6,406,495 B1 | 6/2002 | Schoch |
| 6,406,496 B1 | 6/2002 | Rüter |
| 6,436,144 B1 | 8/2002 | Ahrens |
| 6,436,147 B1 | 8/2002 | Zweymuller |
| 6,454,809 B1 | 9/2002 | Tornier |
| 6,458,136 B1 | 10/2002 | Allard et al. |
| 6,475,243 B1 | 11/2002 | Sheldon et al. |
| 6,488,712 B1 | 12/2002 | Tornier et al. |
| 6,494,913 B1 | 12/2002 | Huebner |
| 6,506,214 B1 | 1/2003 | Gross |
| 6,508,840 B1 | 1/2003 | Rockwood, Jr. et al. |
| 6,514,287 B2 | 2/2003 | Ondrla et al. |
| 6,520,994 B2 | 2/2003 | Nogarin |
| 6,530,957 B1 | 3/2003 | Jack |
| 6,540,770 B1 | 4/2003 | Tornier et al. |
| 6,558,425 B2 | 5/2003 | Rockwood, Jr. |
| 6,569,202 B2 | 5/2003 | Whiteside |
| 6,582,469 B1 | 6/2003 | Tornier |
| 6,589,281 B2 | 7/2003 | Hyde, Jr. |
| 6,599,295 B1 | 7/2003 | Tornier et al. |
| 6,620,197 B2 | 9/2003 | Maroney et al. |
| 6,626,946 B1 | 9/2003 | Walch et al. |
| 6,673,114 B2 | 1/2004 | Hartdegen et al. |
| 6,673,115 B2 | 1/2004 | Resch et al. |
| 6,679,916 B1 | 1/2004 | Frankie et al. |
| 6,699,289 B2 | 3/2004 | Iannotti et al. |
| 6,736,851 B2 | 5/2004 | Maroney et al. |

(56) References Cited

U.S. PATENT DOCUMENTS

| | | |
|---|---|---|
| 6,746,487 B2 | 6/2004 | Seifert et al. |
| 6,749,637 B1 | 6/2004 | Bahler |
| 6,755,866 B2 | 6/2004 | Southworth |
| 6,761,740 B2 | 7/2004 | Tornier |
| 6,767,368 B2 | 7/2004 | Tornier |
| 6,780,190 B2 | 8/2004 | Maroney |
| 6,783,549 B1 * | 8/2004 | Stone ............... A61F 2/4003 623/19.14 |
| 6,790,234 B1 | 9/2004 | Frankle |
| 6,802,864 B2 | 10/2004 | Tornier |
| 6,824,567 B2 | 11/2004 | Tornier et al. |
| 6,863,690 B2 | 3/2005 | Ball et al. |
| 6,875,234 B2 | 4/2005 | Lipman et al. |
| 6,887,277 B2 | 5/2005 | Rauscher et al. |
| 6,890,357 B2 | 5/2005 | Tornier |
| 6,890,358 B2 | 5/2005 | Ball et al. |
| 6,942,699 B2 | 9/2005 | Stone et al. |
| 6,953,478 B2 | 10/2005 | Bouttens et al. |
| 6,969,406 B2 | 11/2005 | Tornier |
| 7,011,686 B2 | 3/2006 | Ball et al. |
| 7,033,396 B2 | 4/2006 | Tornier |
| 7,066,959 B2 | 6/2006 | Errico et al. |
| 7,108,719 B2 | 9/2006 | Horber |
| 7,166,132 B2 | 1/2007 | Callaway et al. |
| 7,169,184 B2 | 1/2007 | Dalla Pria |
| 7,175,663 B1 | 2/2007 | Stone |
| 7,195,645 B2 | 3/2007 | Disilvestro et al. |
| 7,238,207 B2 | 7/2007 | Blatter et al. |
| 7,238,208 B2 | 7/2007 | Camino et al. |
| 7,297,163 B2 | 11/2007 | Huebner |
| 7,309,360 B2 | 12/2007 | Tornier et al. |
| 7,329,284 B2 | 2/2008 | Maroney et al. |
| 7,338,498 B2 | 3/2008 | Long et al. |
| 7,338,528 B2 | 3/2008 | Stone et al. |
| 7,468,077 B2 | 12/2008 | Rochetin et al. |
| 7,544,211 B2 | 6/2009 | Rochetin et al. |
| 7,604,665 B2 | 10/2009 | Iannotti et al. |
| 7,666,522 B2 | 2/2010 | Justin et al. |
| 7,678,150 B2 | 3/2010 | Tornier |
| 7,753,959 B2 | 7/2010 | Berelsman et al. |
| 7,892,287 B2 | 2/2011 | Deffenbaugh |
| 8,002,839 B2 | 8/2011 | Rochetin et al. |
| 8,114,091 B2 | 2/2012 | Ratron et al. |
| 8,231,683 B2 | 7/2012 | Lappin et al. |
| 8,241,365 B2 | 8/2012 | Williams, Jr. et al. |
| 8,303,665 B2 | 11/2012 | Tornier et al. |
| 8,308,807 B2 | 11/2012 | Seebeck et al. |
| 8,465,548 B2 | 6/2013 | Long |
| 8,480,750 B2 | 7/2013 | Long |
| 8,532,806 B1 | 9/2013 | Masson |
| 8,632,597 B2 | 1/2014 | Lappin |
| 8,790,402 B2 | 7/2014 | Monaghan et al. |
| 8,852,283 B2 | 10/2014 | Tornier et al. |
| 8,864,834 B2 | 10/2014 | Boileau et al. |
| 8,961,611 B2 | 2/2015 | Long |
| 9,114,017 B2 | 8/2015 | Lappin |
| 9,351,844 B2 | 5/2016 | Walch et al. |
| 9,545,312 B2 | 1/2017 | Tornier et al. |
| 2001/0032021 A1 | 10/2001 | McKinnon |
| 2001/0047210 A1 | 11/2001 | Wolf |
| 2001/0049561 A1 | 12/2001 | Dews et al. |
| 2002/0032484 A1 | 3/2002 | Hyde, Jr. |
| 2002/0099381 A1 | 7/2002 | Maroney |
| 2002/0138148 A1 | 9/2002 | Hyde, Jr. |
| 2002/0143402 A1 | 10/2002 | Steinberg |
| 2002/0151982 A1 | 10/2002 | Masini |
| 2003/0009170 A1 | 1/2003 | Tornier |
| 2003/0009171 A1 | 1/2003 | Tornier |
| 2003/0028198 A1 | 2/2003 | Tornier et al. |
| 2003/0074072 A1 | 4/2003 | Errico et al. |
| 2003/0097183 A1 | 5/2003 | Rauscher et al. |
| 2003/0114933 A1 | 6/2003 | Bouttens et al. |
| 2003/0125809 A1 | 7/2003 | Iannotti et al. |
| 2003/0149485 A1 | 8/2003 | Tornier |
| 2003/0158605 A1 | 8/2003 | Tornier |
| 2004/0002765 A1 | 1/2004 | Maroney et al. |
| 2004/0006392 A1 | 1/2004 | Grusin et al. |
| 2004/0030394 A1 | 2/2004 | Horber |
| 2004/0034431 A1 | 2/2004 | Maroney et al. |
| 2004/0039449 A1 | 2/2004 | Tornier |
| 2004/0064189 A1 | 4/2004 | Maroney et al. |
| 2004/0064190 A1 | 4/2004 | Ball et al. |
| 2004/0133276 A1 | 7/2004 | Lang et al. |
| 2004/0134821 A1 | 7/2004 | Tornier |
| 2004/0138754 A1 | 7/2004 | Lang et al. |
| 2004/0148033 A1 | 7/2004 | Schroeder |
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0210217 A1 | 10/2004 | Baynham et al. |
| 2004/0210317 A1 | 10/2004 | Maroney et al. |
| 2004/0215200 A1 | 10/2004 | Tornier et al. |
| 2004/0220673 A1 | 11/2004 | Pria |
| 2004/0220674 A1 | 11/2004 | Pria |
| 2004/0225367 A1 | 11/2004 | Glien et al. |
| 2004/0230197 A1 | 11/2004 | Tornier et al. |
| 2004/0210220 A1 | 12/2004 | Tornier |
| 2004/0267370 A1 | 12/2004 | Ondria |
| 2005/0008672 A1 | 1/2005 | Winterbottom et al. |
| 2005/0015154 A1 | 1/2005 | Lindsey et al. |
| 2005/0043805 A1 | 2/2005 | Chudik |
| 2005/0049709 A1 | 3/2005 | Tornier |
| 2005/0055102 A1 | 3/2005 | Tornier et al. |
| 2005/0065612 A1 | 3/2005 | Winslow |
| 2005/0085919 A1 | 4/2005 | Durand-Allen et al. |
| 2005/0085921 A1 | 4/2005 | Gupta et al. |
| 2005/0090902 A1 | 4/2005 | Masini |
| 2005/0107882 A1 | 5/2005 | Stone et al. |
| 2005/0113931 A1 | 5/2005 | Horber |
| 2005/0119531 A1 | 6/2005 | Sharratt |
| 2005/0143829 A1 | 6/2005 | Ondria et al. |
| 2005/0165490 A1 | 7/2005 | Tornier |
| 2005/0177241 A1 | 8/2005 | Angibaud et al. |
| 2005/0197708 A1 | 9/2005 | Stone et al. |
| 2005/0203536 A1 | 9/2005 | Laffargue et al. |
| 2005/0209700 A1 | 9/2005 | Rockwood et al. |
| 2005/0216092 A1 | 9/2005 | Marik et al. |
| 2005/0251263 A1 | 11/2005 | Forrer et al. |
| 2005/0256584 A1 | 11/2005 | Farrar |
| 2005/0267590 A1 | 12/2005 | Lee |
| 2005/0278031 A1 | 12/2005 | Tornier et al. |
| 2005/0278032 A1 | 12/2005 | Tornier et al. |
| 2005/0278033 A1 | 12/2005 | Tornier et al. |
| 2005/0288681 A1 | 12/2005 | Klotz et al. |
| 2005/0288791 A1 | 12/2005 | Tornier et al. |
| 2006/0004462 A1 | 1/2006 | Gupta |
| 2006/0009852 A1 | 1/2006 | Winslow et al. |
| 2006/0015185 A1 | 1/2006 | Chambat |
| 2006/0020344 A1 | 1/2006 | Schultz et al. |
| 2006/0030946 A1 | 2/2006 | Ball et al. |
| 2006/0074353 A1 | 4/2006 | Deffenbaugh et al. |
| 2006/0122705 A1 | 6/2006 | Morgan |
| 2006/0149388 A1 | 7/2006 | Smith et al. |
| 2006/0173457 A1 | 8/2006 | Tornier |
| 2006/0235538 A1 | 10/2006 | Rochetin et al. |
| 2006/0241775 A1 | 10/2006 | Buss |
| 2007/0016304 A1 | 1/2007 | Chudik |
| 2007/0142918 A1 | 6/2007 | Stone |
| 2007/0225817 A1 | 9/2007 | Reubelt et al. |
| 2007/0225818 A1 | 9/2007 | Reubelt et al. |
| 2007/0225821 A1 | 9/2007 | Reubelt et al. |
| 2007/0244564 A1 | 10/2007 | Ferrand et al. |
| 2007/0250174 A1 | 10/2007 | Tornier et al. |
| 2008/0195108 A1 | 8/2008 | Bhatnagar et al. |
| 2009/0149961 A1 | 6/2009 | Dallmann |
| 2010/0016975 A1 | 1/2010 | Iannotti et al. |
| 2010/0161066 A1 | 6/2010 | Iannotti et al. |
| 2010/0217399 A1 | 8/2010 | Groh |
| 2011/0190899 A1 | 8/2011 | Pierce et al. |
| 2013/0110470 A1 | 5/2013 | Vanasse et al. |
| 2013/0253656 A1 | 9/2013 | Long |
| 2013/0261752 A1 | 10/2013 | Lappin et al. |
| 2014/0142711 A1 | 5/2014 | Maroney et al. |
| 2014/0257499 A1 | 9/2014 | Winslow et al. |

(56) References Cited

U.S. PATENT DOCUMENTS

| | | |
|---|---|---|
| 2014/0371863 A1 | 12/2014 | Vanasse et al. |
| 2015/0150688 A1 | 6/2015 | Vanasse et al. |
| 2016/0242921 A1 | 8/2016 | Walch et al. |
| 2017/0095336 A1 | 4/2017 | Tornier et al. |

FOREIGN PATENT DOCUMENTS

| | | | |
|---|---|---|---|
| CN | 101340862 A | 1/2009 | |
| DE | 19509037 C1 | 9/1996 | |
| DE | 19630298 | 1/1998 | |
| EP | 0299889 B1 | 1/1989 | |
| EP | 0257359 B1 | 11/1991 | |
| EP | 0524857 | 1/1993 | |
| EP | 0617934 A1 | 10/1994 | |
| EP | 0549480 B1 | 8/1997 | |
| EP | 0599429 B1 | 10/1997 | |
| EP | 0797964 A1 | 10/1997 | |
| EP | 0679375 B1 | 9/1998 | |
| EP | 0864306 A2 | 9/1998 | |
| EP | 0712617 B1 | 9/1999 | |
| EP | 0715836 B1 | 10/2001 | |
| EP | 0664108 B1 | 8/2002 | |
| EP | 0809986 B1 | 10/2002 | |
| EP | 0927548 B1 | 5/2003 | |
| EP | 0807426 B1 | 10/2003 | |
| EP | 1380274 A1 | 1/2004 | |
| EP | 1402854 B1 | 3/2004 | |
| EP | 0903128 B1 | 5/2004 | |
| EP | 1195149 B1 | 7/2005 | |
| EP | 1064890 B1 | 9/2005 | |
| EP | 1607067 A1 | 12/2005 | |
| EP | 1062923 B9 | 7/2006 | |
| EP | 1782765 A1 | 5/2007 | |
| EP | 0903127 B1 | 6/2007 | |
| EP | 1844737 A2 * | 10/2007 | ........... A61F 2/4081 |
| EP | 1515758 B1 | 3/2009 | |
| EP | 1639966 B1 | 9/2009 | |
| EP | 1902689 B1 | 11/2011 | |
| EP | 1996125 B1 | 5/2013 | |
| EP | 2335655 B1 | 7/2013 | |
| EP | 1973498 B1 | 4/2014 | |
| EP | 1844737 B1 | 6/2015 | |
| FR | 2248820 A1 | 5/1975 | |
| FR | 2545352 | 11/1984 | |
| FR | 2574283 | 6/1986 | |
| FR | 2652498 | 4/1991 | |
| FR | 2664809 | 1/1992 | |
| FR | 2699400 | 6/1994 | |
| FR | 2721200 | 12/1995 | |
| FR | 2726994 | 5/1996 | |
| FR | 2737107 | 1/1997 | |
| FR | 2835425 | 8/2003 | |
| FR | 2836039 | 8/2003 | |
| FR | 2848099 A1 | 6/2004 | |
| FR | 2848099 A1 * | 6/2004 | ............... A61F 2/40 |
| JP | 2009-513285 | 4/2009 | |
| SU | 749392 | 7/1980 | |
| WO | WO 91/07932 | 6/1991 | |
| WO | WO 93/09733 | 5/1993 | |
| WO | WO 96/17553 | 6/1996 | |
| WO | WO 97/025943 | 7/1997 | |
| WO | WO 98/46172 | 10/1998 | |
| WO | WO 99/49792 | 10/1999 | |
| WO | WO 99/65413 | 12/1999 | |
| WO | WO 00/15154 | 3/2000 | |
| WO | WO 00/41653 | 7/2000 | |
| WO | WO 01/47442 | 7/2001 | |
| WO | WO 02/039931 | 5/2002 | |
| WO | WO 02/039933 | 5/2002 | |
| WO | WO 02/067821 | 9/2002 | |
| WO | WO 03/005933 | 1/2003 | |
| WO | WO 03/094806 | 11/2003 | |
| WO | WO 03/101320 | 12/2003 | |
| WO | WO 07/109291 | 9/2007 | |
| WO | WO 07/109319 | 9/2007 | |
| WO | WO 07/109340 | 9/2007 | |
| WO | WO 2015/068035 | 5/2015 | |

OTHER PUBLICATIONS

"Aequalis-Glenoid Keeled and Pegged—Surgical Technique Brochure," Tornier, Inc., 2003 in 12 pages.

"Aequalis-Reversed™ Shoulder Prosthesis, Surgical Technique," Tornier, Inc., 2004, in 24 pages.

"Anatomic Glenoid, Surgical Technique," Smith & Nephew, Inc., Feb. 2000 in 6 pages.

"Anatomical Shoulder™—Cemented Shoulder Prosthesis Product Information and Surgical Technique," Sulzer Medica, 2000, in 30 pages.

"Anatomical Shoulder™—System—The new removable head option," Zimmer Inc., 2004 in 6 pages.

"Anatomical Shoulder™—System Surgical Technique—Removable head option for improved surgical results," Zimmer, Inc., 2004, in 33 pages.

Apoil, A., "A Condyle for the Rotator Cuff Muscles: The Total Shoulder Prosthesis," Aesculap—ICP S.A., Feb. 1994, in 4 pages.

Bigliani/Flatow®—The Complete Shoulder Solution, Designed by Shoulder Surgeons for Shoulder Surgery, Zimmer, Inc., 2001 in 6 pages.

"Bigliani/Flatow®—The Complete Shoulder Solution, Total Shoulder Arthroplasty Surgical Technique," Zimmer, Inc., 2003, in 30 pages.

Bigliani/Flatow®—The Complete Shoulder Solution, 4-Part Fracture of the Humerus Surgical Technique, Zimmer, Inc., 2001.

"Bio-Modular® / Bi-Polar Shoulder Arthroplasty," Biomet, Inc., 1997, in 2 pages.

"Bio-Modular® Choice—Shoulder System—Surgical Technique," Biomet Orthopedics, Inc., 2004, in 16 pages.

Boileau, P., et al. "Adaptability and modularity of shoulder prosthese," Maitrise Orthopédique, https://www.maitriseorthop.com/corpusmaitri/orthopaedic/prothese_epaule_orthop/boileau_us.shtml, downloaded Jan. 3, 2006.

Boileau, P., et al. "Arthroscopic Repair of Full-Thickness Tears of the Supraspinatus: Does the Tendon Really Heal?" The Journal of Bone and Joint Surgery, Inc., Jun. 2005, 87A(6): 1229-1240.

Boileau, P., "Technique de synthèse des tubérosités," Tornier, Inc., 2005, in 2 pages.

Boileau, P., "The technique of Tuberosities Fixation," Tornier, Inc., 2007, in 2 pages.

Buechel, F.F., "Buechel-Pappas™ Modular Salvage Shoulder System, Surgical Procedure," Endotec, Inc., Aug. 2001, in 8 pages.

Buechel, F.F., "Buechel-Pappas™ Resurfacing Shoulder System, Surgical Procedure" Endotec, Inc., Aug. 2000, in 8 pages.

Buechel, F.F., "Buechel-Pappas™ Total Shoulder System, Surgical Procedure," Endotec, Inc., Aug. 2000, in 16 pages.

Cofield, R.H., "Cofield[2] Total Shoulder System, Surgical Technique," Smith & Nephew, 1997, in 32 pages.

"Copeland™ Humeral Resurfacing Head," Biomet Orthopedics, Inc., 2001, in 12 pages.

"Delta CTA™ Reverse Shoulder Prosthesis—Surgical Technique," DePuy International Ltd., revised Aug. 2004, in 28 pages.

Fenlin, Jr., J.M., "Total Glenohumeral Joint Replacement," Symposium on Surgery of the Shoulder, Orthopedic Clinics of North America, Apr. 1975, 6(2): 565-583.

"Global C.A.P.™ Surgical Technique, Resurfacing Humeral Head Implant," DePuy International, Ltd., revised Oct. 2004, in 23 pages.

Hertel, R., "Technical considerations for implantation of EPOCA glenoid components (Leseprobe)," Epoca Newsletter, May 14, 2001, in 1 page.

Search Report and Written Opinion issued in EP 11185537.5 dated Feb. 14, 2012, in 5 pages.

Klein, T.J., et al., "Mechanically Favorable Bone Remodeling in Rotator Cuff Arthropathy Patients with Good Function," presented at the 23rd Annual Meeting of the American Society of Biomechanics University of Pittsburgh, Oct. 21-23, 1999, in 2 pages.

(56) References Cited

OTHER PUBLICATIONS

"Latitude Total Elbow Prosthesis Surgical Technique," Tornier Implants, 2004, in 40 pages.
"Latitude Total Elbow Prosthesis Surgical Technique," Tornier Implants, 2007, in 44 pages.
Mansat, M., "Neer 3™, Surgical Technique for Fractures," Smith & Nephew, Sep. 2000, in 19 pages.
Nicholson, G.P., "Chapter 7: Arthroplasty and Rotator Cuff Deficiency," Shoulder Arthroplasty, 2005, pp. 149-166.
"Offset Head: Bio-Modular® Total Shoulder," Biomet, Inc. 2000 in 2 pages.
"The FOUNDATION® Total Shoulder System," Encore Orthopedics, Inc., Apr. 1996, in 3 pages.
"FDA Summary of Safety and Effectiveness: Glenoid Component for the FoundationTM Total Shoulder System," Encore Orthopedics, Inc., Apr. 15, 1996, in 1 page.
"Tornier Surgical Technique Addendum, Aequalis® Reversed Shoulder Polyethylene Insert," Tornier, Inc., Oct. 8, 2005, in 1 page.
"Zimmer® Shoulder Retractors," Zimmer, Inc., 2000, in 2 pages.

\* cited by examiner

SET OF GLENOID COMPONENTS FOR A SHOULDER PROSTHESIS

CROSS-REFERENCE TO RELATED APPLICATION

This application is a continuation of U.S. application Ser. No. 15/145,210, filed Oct. 21, 2011, now U.S. Pat. No. 10,631,993 which is a divisional of U.S. patent application Ser. No. 13/279,070, now U.S. Pat. No. 9,351,844, filed on Oct. 21, 2011, which claims the benefit of U.S. Provisional Patent Application Ser. No. 61/488,102, filed on May 19, 2011, and claims foreign priority to French Patent Application No. FR1058647, filed on Oct. 22, 2010, all of which are incorporated by reference herein in their entireties for all purposes.

TECHNICAL FIELD

Embodiments of the present invention relate to a set of glenoid components for a shoulder prosthesis.

BACKGROUND

Typically, the body of a glenoid component is not very thick, the two opposite primary faces of said body respectively being adapted to cooperate in a ball-and-socket manner with a humeral head, either natural or prosthetic, and to be pressed against the socket of a shoulder blade so as to be immobilized there. To that end, the first aforementioned face includes a joint surface, generally spherical, while the second face includes a bearing surface, which is also spherical or planar, in the central region of which often at least one bone anchoring element protrudes in the socket, such as a keel or pins. Such glenoid components may be provided in different sizes, but the glenoid components of different sizes often have identical bearing surfaces.

Thus, depending in particular on the patient's morphology, the surgeon has the option of choosing the glenoid component of which the size seems best suited to the patient. As a result, the articular performance of the patient's prosthetic shoulder is quite often satisfactory. At the same time, it has, however, been observed that, during use of glenoid components which did not best suit the patient, the implanted glenoid component tends gradually to come unsealed from the socket, through wear or mechanical alteration of the interface between the body and the socket.

SUMMARY

A set of glenoid components for use in a joint according to embodiments of the present invention includes a first glenoid component having a first joint surface and a first bearing surface, and a second glenoid component having a second joint surface and a second bearing surface, wherein each of the first and second joint surfaces is configured to cooperate with a prosthetic or natural bone head, wherein each of the first and second bearing surfaces is configured for placement against a socket of the joint, wherein the first joint surface is substantially the same as the second joint surface, and wherein the first and second bearing surfaces have different dimensional geometries. Both the first and second bearing surfaces may include substantially convex curved surfaces. The first bearing surface may have a first radius of curvature, and the second bearing surface may have a second radius of curvature that is greater than the first radius of curvature. The second radius of curvature is at least 4 mm greater, or 8 mm greater, than the first radius of curvature, according to embodiments of the present invention.

According to some embodiments of the present invention, the first and second glenoid components are of a first size, and the set further includes a third glenoid component having a third joint surface and a third bearing surface, a fourth glenoid component having a fourth joint surface and a fourth bearing surface, wherein each of the third and fourth joint surfaces is also configured to cooperate with the prosthetic or natural bone head, wherein each of the third and fourth bearing surfaces is also configured for placement against the socket of the joint, wherein the third and fourth glenoid components are of a second size larger than the first size, wherein the third joint surface is substantially the same as the fourth joint surface, and wherein the third and fourth bearing surfaces have different dimensional geometries. The first bearing surface may have a first radius of curvature, the second bearing surface may have a second radius of curvature that is greater than the first radius of curvature, the third bearing surface may have a third radius of curvature, and the fourth bearing surface may have a fourth radius of curvature that is greater than the third radius of curvature, according to embodiments of the present invention. In some cases, the first radius of curvature may be the same as the third radius of curvature. In such cases, the second radius of curvature may be the same as the fourth radius of curvature. In other cases, the first radius of curvature may be smaller than the third radius of curvature, and/or the second radius of curvature may be smaller than the fourth radius of curvature.

According to some embodiments of the present invention, the first and third bearing surfaces have identical dimensional geometries. According to other embodiments of the present invention, the different dimensional geometries are two different geometries selected from the group including a planar surface, a convex curved surface, a concave curved surface, and a terraced surface. At least one of the first and second bearing surfaces may include a protruding anchor element configured for engagement with the socket of the joint.

According to some embodiments of the present invention, the first glenoid component includes a first top face and a first bottom face, the first top face including the first joint surface, the first bottom face including the first bearing surface, wherein the first bearing surface occupies most or all of the first bottom face other than an anchor element, if any. According to some embodiments of the present invention, the joint is a shoulder joint, the socket is a shoulder blade socket, and the prosthetic or natural bone head is a prosthetic or natural humeral head.

A set according to embodiments of the present invention may further include a fifth glenoid component having a fifth joint surface and a fifth bearing surface, and a sixth glenoid component having a sixth joint surface and a sixth bearing surface, wherein each of the fifth and sixth joint surfaces is also configured to cooperate with the prosthetic or natural bone head, wherein each of the fifth and sixth bearing surfaces is also configured for placement against the socket of the joint, wherein the fifth and sixth glenoid components are of a third size larger than the second size, wherein the fifth joint surface is substantially the same as the sixth joint surface, and wherein the fifth and sixth bearing surfaces have different dimensional geometries. According to such embodiments, the first, second, third, fourth, fifth, and sixth glenoid components may be packaged together in a kit, for example within a common box or container.

According to some embodiments of the present invention, the first bearing surface has a first radius of curvature, the second bearing surface has a second radius of curvature that is greater than the first radius of curvature, the third bearing surface has a third radius of curvature, the fourth bearing surface has a fourth radius of curvature that is greater than the third radius of curvature, the fifth bearing surface has a fifth radius of curvature, and the sixth bearing surface has a sixth radius of curvature that is greater than the fifth radius of curvature. The first radius of curvature may be the same as the third radius of curvature but less than the fifth radius of curvature; and/or the second radius of curvature may be the same as the fourth radius of curvature but less than the sixth radius of curvature, according to embodiments of the present invention. In some cases, the fifth radius of curvature is at least 4 mm smaller, or at least 8 mm smaller, than the sixth radius of curvature.

A method for glenoid implantation according to embodiments of the present invention includes evaluating a geometrical shape of a patient's bone socket, selecting a glenoid component from a set of glenoid components, the set of glenoid components including at least two different sizes of glenoid components, with at least two glenoid components of each size having geometrically different bearing surfaces but similar joint surfaces, wherein selecting the glenoid component includes first selecting a size of the at least two different sizes, and then within the selected size selecting a best match of the geometrically different bearing surface with the geometrical shape of the patient's bone socket, and implanting the selected glenoid component in the patient's bone socket.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
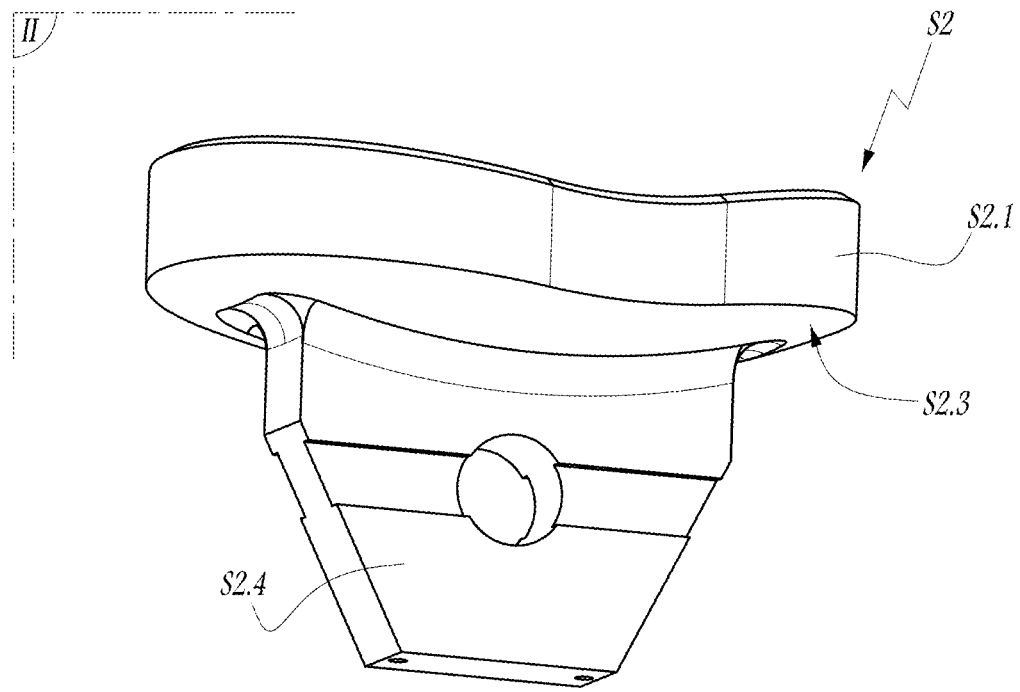
FIG. 1 illustrates a perspective view of a glenoid component of a set of glenoid components, according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

A set of glenoid implants according to embodiments of the present invention allows the surgeon to improve the durability of the mechanical cooperation between the implanted glenoid component and the socket of the patient. As such, embodiments of the present invention include a set of glenoid components of a shoulder prosthesis, including glenoid components that each include a body defining, on two of its opposite faces, respectively, a joint surface, intended to cooperate with a humeral head, prosthetic or natural, and a bearing surface bearing against the socket of a shoulder blade, in which set the glenoid components are provided in several different sizes, respectively defined by the dimensions of their respective joint surfaces, the set being characterized in that, in each size, at least two glenoid components are provided with bearing surfaces respectively having different dimensional geometries.

According to one embodiment of the present invention, the surgeon is provided with different sized glenoid components (e.g. at least two different sizes), each of which are available with respective support surfaces provided to be different from each other. In this way, to place a prosthesis in the shoulder of a given patient, the surgeon decides on the size of the glenoid component based on considerations related to the joint to be reestablished with the patient's humeral head, prosthetic or natural, then, given the size that the surgeon has selected, the surgeon chooses the glenoid component with the bearing surface best suited to the patient's glenoid, in its natural actual size or after having surgically prepared it. During surgery, the surgeon strives to keep the greatest possible amount of bone material actually present. Thus, use of embodiments of the present invention is counterintuitive to traditional dogma, according to which the surgeon must perform fairly substantial bone preparation operations for the patient's socket by removing a significant quantity of bone matter from the shoulder blade, to shape, in the patient's shoulder blade, a glenoid cavity adapted to the unique geometry and imposed on the glenoid bearing surface of the component that the surgeon has chosen by its size, e.g., as a function of its joint surface. Conversely, while leaving the surgeon the choice of a size for the glenoid component to be implanted, the glenoid component according to embodiments of the present invention allows the surgeon to take into account the actual state of the patient's glenoid. Furthermore, the bone state of patients' sockets varies within non-negligible proportions, in a manner not correlated to the joint cooperation to be reestablished using a shoulder prosthesis, according to embodiments of the present invention.

According to embodiments of the present invention, the differences between the bearing surfaces of the different glenoid components of a same size can follow the overall geometric size of these surfaces, or, for a given geometric shape, the dimensions of said geometric shape. Of course, the number of sizes present in the set according to embodiments of the invention as well as, within a same size, the number of glenoid components having different respective bearing surfaces, can be as large as desired.

Embodiments of a glenoid component may include a combination of one or more of the following features and/or characteristics, according to embodiments of the present invention:

the dimensional geometries, respectively provided to be different for at least two of the glenoid components having a same size, correspond to a same convex curved surface shape but have as many different curves;

the same convex curved surface shape is substantially spherical, so that said dimensional geometries, respectively provided to be different for at least two of the glenoid components having a same size, correspond to as many different curve radii;

for at least some sizes, the difference between the respective curve radii of the bearing surfaces of said at least two components having a same size is greater than 4 mm, or in some cases greater than 8 mm;

at least one of the curve radii, respectively provided to be different for a same size, has a value that is unchanged at least once when, among the sizes, one goes from a smaller size to a larger size;

at least one of the curve radii, respectively provided to be different for a same size, has a value that increases at least once when, among the sizes, one goes from a smaller size to a larger size;

the dimensional geometries, respectively provided to be different for at least two of the glenoid components having a same size, correspond to as many different geometric shapes selected from the group consisting of: a planar surface, a convex curved surface, a concave curved surface, and a terraced surface;

at least one of said dimensional geometries, respectively provided to be different for at least two of the glenoid components having a same size, is found identically in at least two of the different sizes;

at least one of the glenoid components of the set is provided with at least one anchor element in the socket of the shoulder blade, which protrudes from the bearing surface of said glenoid component;

the bearing surface of each of the glenoid components of the set occupies, outside the anchoring element(s) that may be present, most or all of the corresponding face of the body of the glenoid component.

Figure 2:
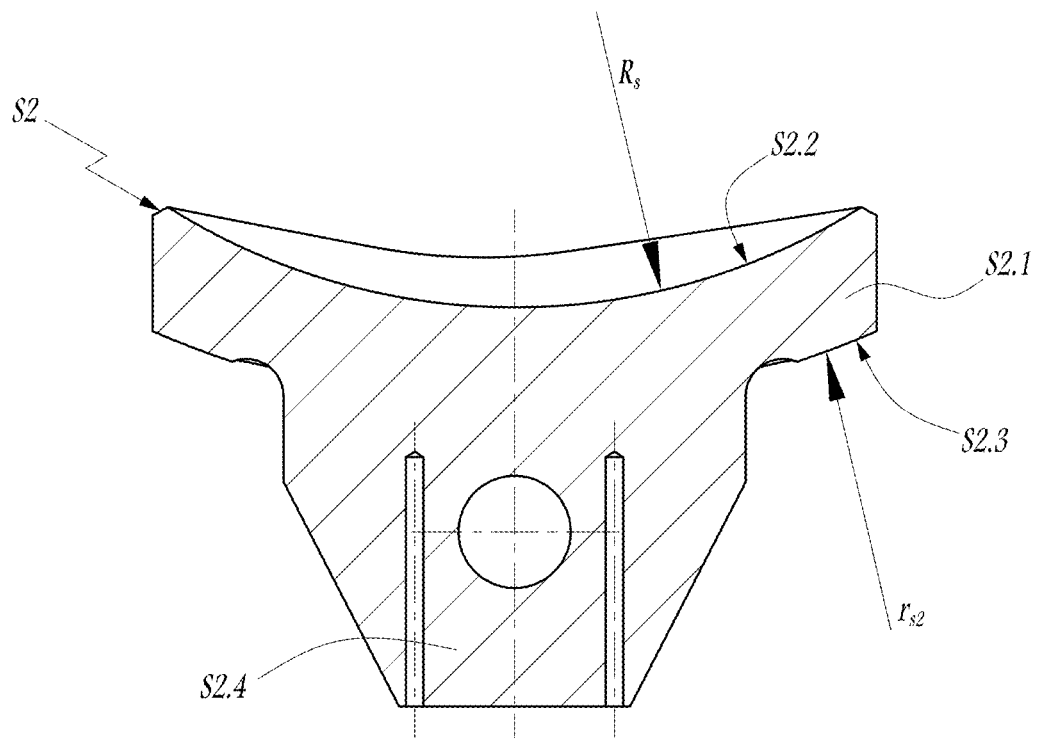
FIG. 2 illustrates a cross-sectional view of the glenoid component of FIG. 1 along plane II of FIG. 1, according to embodiments of the present invention.

FIGS. 1 and 2 show a glenoid prosthesis component S2. This component S2 has a primary body S2.1 that has sides, in two spatial dimensions, that are significantly larger than its side in its third spatial dimension, this third side thus corresponding to the thickness of the body. The body S2.1 therefore has two opposite primary faces, connected by a peripheral face embodying the aforementioned thickness of the body.

The body S2.1 can also be a single piece, as shown in FIGS. 1 and 2, or correspond to the fixed assembly of several parts. Furthermore, the body S2.1 is made from one or more materials having a suitable rigidity and strength to, as described in more detail below, both cooperate with a humeral head (not shown) and be securely fixed to the bone socket of a shoulder blade (also not shown in the figures).

One of the two aforementioned primary faces of the body S2.1 defines a joint surface S2.2 shaped to engage with the substantially complementary surface of the aforementioned humeral head. In practice, this humeral head is either natural, e.g. it corresponds to the natural upper epiphysis of the humerus associated with the shoulder blade, or prosthetic, e.g. it is defined by a humeral component of a shoulder prosthesis to which the glenoid component S2 belongs.

The joint surface S2.2 of the body S2.1 is substantially spherical, according to embodiments of the present invention. The corresponding curve radius is denoted $R_S$. In the glenoid component shown in FIGS. 1 and 2, this joint surface S2.2 is concave. As a non-illustrated alternative, this joint surface may be convex. The joint surface S2.2 may occupy most of the corresponding face of the body S2.1, or all of said face, as for example illustrated in FIGS. 1 and 2, according to embodiments of the present invention. The other primary face of the body S2.1 is adapted to be securely fastened to the aforementioned socket. To that end, this face includes a bearing surface S2.3 on the socket, from the central region from which an anchoring keel S2.4 for anchoring in the socket extends. According to embodiments of the present invention, outside the anchor keel S2.4, the bearing surface S2.3 advantageously occupies most of the corresponding face of the body S2.1, or all of that face, as for example in the glenoid component illustrated in the figures.

As a non-illustrated alternative, bone anchoring elements other than the keel S2.4 can be provided, to replace or complement said keel. Likewise, such anchor elements can be completely absent, according to embodiments of the present invention. In the glenoid component shown in FIGS. 1 and 2, the bearing surface S2.3 of the body S2.1 is substantially spherical, in other words, it corresponds to a sphere portion for which the curve radius is denoted $r_{S2}$. The surfaces S2.2 and S2.3 may or may not be concentric. In the event they are not concentric, their respective geometric center may or may not be situated in a same median plane of the body S2.1, according to embodiments of the present invention.

Figure 3:
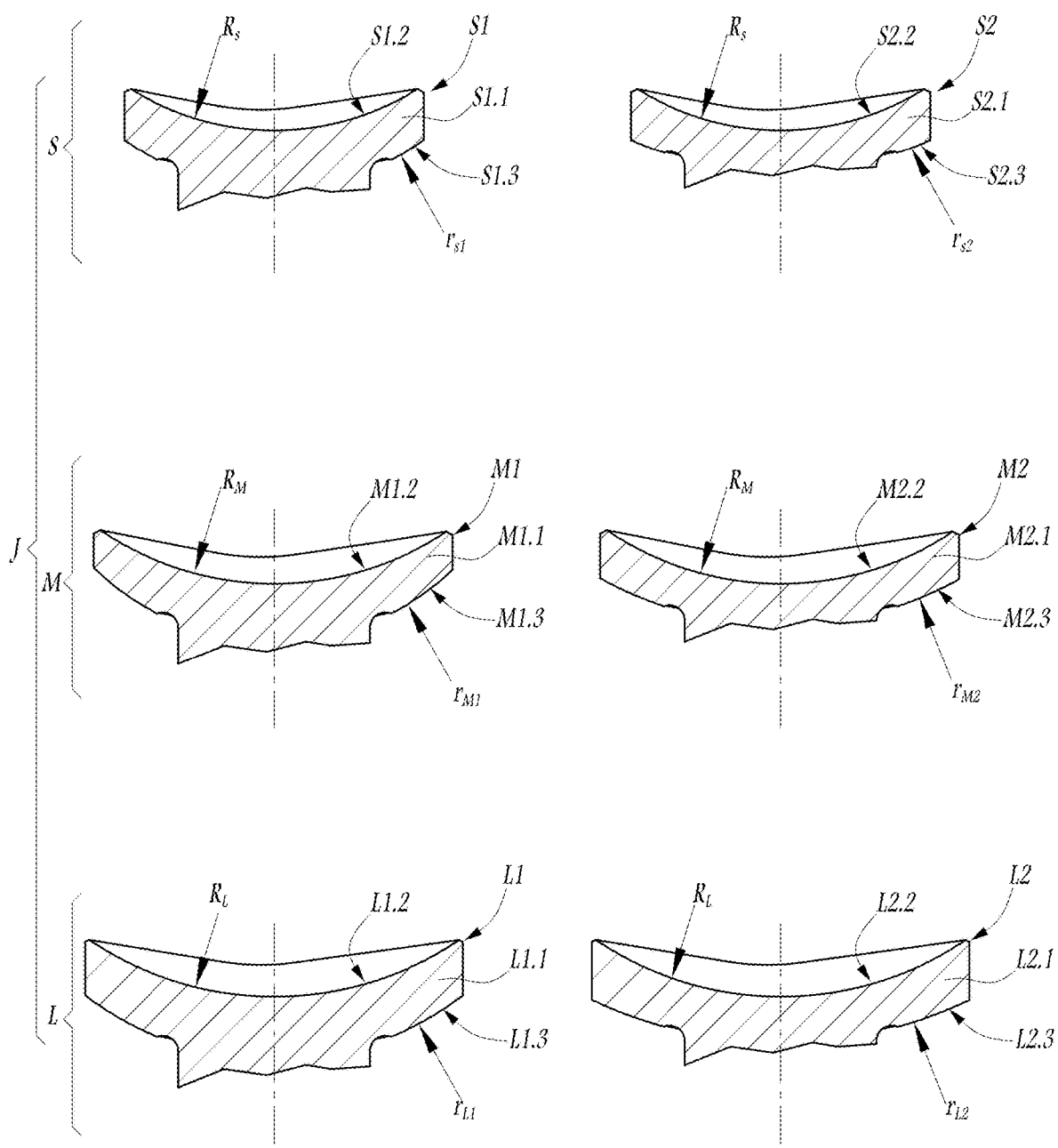
FIG. 3 illustrates a set of glenoid components, according to embodiments of the present invention.

According to some embodiments of the invention, the glenoid component S2, which is described in detail above with respect to FIGS. 1 and 2, belongs to a set J of six glenoid components, as shown in FIG. 3. Thus, in addition to the glenoid component S2, which appears in the upper right corner of FIG. 3, the set J comprises five other glenoid components, respectively referenced S1, M1, M2, L1 and L2.

Each of the components S1, M1, M2, L1 and L2 comprises a body S1.1, M1.1, M2.1, L1.1 and L2.1, which is functionally similar to the body S2.1 of the component S2. In particular, each body S1.1, M1.1, M2.1, L1.1, L2.1 has, opposite one another, a joint surface S1.2, M1.2, M2.2, L1.2 and L.2, functionally similar to the joint surface S2.2 of the component S2, and a bearing surface S1.3, M1.3, M2.3, L1.3, L2.3 functionally similar to the bearing surface S2.3 of the component S2.

Component S1 is the same size as component S2, in that their respective joint surfaces S1.2 and S2.2 have substantially the same dimensions. In particular, as shown in FIG. 3, these joint surfaces S1.2 and S2.2 are substantially spherical and have the same curve radius $R_S$ according to embodiments of the present invention. The components S1 and S2 thus form, within the set J, a group of size S. According to some embodiments of the present invention, the joint surfaces S1.2 and S2.2 are identical or have curved surfaces which are identical.

On the other hand, component S1 differs from component S2 by the dimensional geometry of its bearing surface S1.3 compared to that of the bearing surface S2.3 of component S2. In other words, the bearing surfaces S1.3 and S2.3 both have the same sphere portion shape, but their respective curve radii $r_{S1}$ and $r_{S2}$ are different: $r_{S1}$ is smaller than $r_{S2}$, according to embodiments of the present invention.

Likewise, components M1 and M2 are the same size and thus form, within the set J, a group of two components, referenced M in FIG. 3. By comparison to components S1 and S2, the joint surfaces M1.2 and M2.2 of components M1 and M2 have substantially the same dimensions, in particular, in the illustrated example, the same curve radius $R_M$. The group of size M, containing components M1 and M2, differs from group S, containing components S1 and S2, in that the radius $R_M$ has a value greater than that of the radius $R_S$, according to embodiments of the present invention.

Furthermore, as for components S1 and S2 in the group of size S, the bearing surfaces M1.3 and M2.3 of components M1 and M2 of the group of size M have different dimensional geometries, e.g. these bearing surfaces are both sphere portions for which the respective radii $r_{M1}$ and $r_{M2}$ are different, the value of the radius $r_{M1}$ being smaller than the value of the radius $r_{M2}$.

The radii $r_{S1}$ and $r_{M1}$ illustrated in FIG. 3 may have the same value and the radii $r_{S2}$ and $r_{M2}$ may also have the same value, according to embodiments of the present invention. In other words, when one goes from the group of size S to the group of size M, the curve radii $r_{S1}$ and $r_{M1}$ of the bearing surfaces S1.3 and M1.3 have an unchanged value, according to embodiments of the present invention. The same may be true for the bearing surfaces S2.3 and M2.3, according to embodiments of the present invention.

Lastly, by transposition of the preceding technical considerations relative to the components S1 and S2 of the group of size S and components M1 and M2 of the group of size M, components L1 and L2 constitute a group of size L, such that:

the joint surfaces L1.2 and L2.2 of the components L1 and L2 have substantially the same dimensions, in particular the same curve radius $R_L$, which has a value strictly greater than that of the radius $R_M$, according to embodiments of the present invention, and the bearing surfaces L1.3 and L2.3 are both sphere portions having respective curve radii $r_{L1}$ and $r_{L2}$, the radius $r_{L1}$ having a value below that of the radius $r_{L2}$, according to embodiments of the present invention.

The radius $r_{L1}$ may have a value greater than that of the radius $r_{M1}$, but smaller than that of the radius $r_{M2}$, according to embodiments of the present invention. And the radius $r_{L2}$ may have a value greater than that of the radius $r_{M2}$, according to embodiments of the present invention.

The radii of curvature $R_S$, $R_M$ and $R_L$ may not only increase from size S to size M to size L, but the joint surfaces of the glenoid components of each of the groups with the same size may also differ by an increase in edge-to-edge expanse, for example in the plane of FIG. 3, according to embodiments of the present invention. This difference in the edge-to-edge expanse is optional, however, and is not present in all embodiments of glenoid component sets, according to embodiments of the present invention.

The glenoid components of the set J are broken down into three groups of different sizes: S, M and L, according to embodiments of the present invention. Depending on whether the surgeon chooses one of components S1 and S2 or one of components M1 and M2 or one of components L1 and L2, the joint behavior of the selected glenoid component, relative to the humeral head of the patient, is fixed. However, for each of sizes S, M and L, the surgeon's choice of one of the two available components allows him to account for the actual state of the patient's socket: in particular, the surgeon will choose the one of the two available components for which the curvature of the bearing surface is best suited to the actual geometric configuration of the socket, in particular to limit the extent of the prior preparation of the socket, thereby limiting the loss of bone substance, while also optimizing the extent of the bearing interface produced between the socket and the component selected during implantation thereof, according to embodiments of the present invention.

The difference between the radii of curvature of the bearing surfaces of the components of a same size is, for example, greater than or equal to 4 mm, according to embodiments of the present invention. According to other embodiments of the present invention, the difference between the radii of curvature of the bearing surfaces of the components of a same size is greater than or equal to 8 mm.

Thus, one non-limiting example of numerical quantification related to the embodiment of the set J shown in FIG. 3 is as follows:
$r_{S1}$=34 mm,
$r_{S2}$=38 mm,
$r_{M1}$=34 mm,
$r_{M2}$=38 mm,
$r_{L1}$=36 mm, and
$r_{L2}$=44 mm.

Various arrangements and alternatives may be utilized for the set of glenoid components J. As one example, at least one of the three groups of different sizes S, M and L may include more than two glenoid components, the respective bearing surfaces of the at least three glenoid components respectively having different dimensional geometries. Likewise, the set can be provided with only two groups of different sizes, for example S and M, or S and L or M and L, according to embodiments of the present invention. The set can also include more than three groups of different sizes, according to embodiments of the present invention.

According to one alternative embodiment of the present invention (not shown), the difference of dimensional geometries between the bearing surfaces of the glenoid components of a same size does not correspond to a dimensional difference of a same geometric shape, as is the case for the set J, but this difference is based on the presence of as many different geometric shapes as there are glenoid components present in the group of a same size. In other words, within each group of a same size, one of the glenoid components has, for example, a planar bearing surface while the other glenoid component has a bearing surface with a convex curve, according to embodiments of the present invention. More generally, the respective bearing surfaces of the at least two glenoid components present in the aforementioned group then have different geometric shapes that are chosen from among at least a planar surface, a convex curved surface, a concave curved surface and a terraced surface, according to embodiments of the present invention.

Optionally, rather than being continuously smooth as in the figures, the bearing surfaces of the components of the set J can have a roughness, or even macro-aspects, such as grooves, pyramidal spurs, conical cells, and the like, to strengthen the immobilization of the component in the socket.

Although embodiments of the present invention are described with respect to shoulder joints, one of ordinary skill in the art, based on the disclosure provided herein, will recognize that similar sets of glenoid components may be used for other joints, for example hip joints, according to embodiments of the present invention.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A set of glenoid components for use in a shoulder joint, the set comprising:

a first glenoid component comprising a first primary body and a first anchoring element, the first primary body comprising a first joint surface configured to cooperate with a prosthetic or natural bone head and a first bearing surface configured for placement against the patient's shoulder blade socket, the first anchoring element extending from the first bearing surface; and a second glenoid component comprising a second primary body and a second anchoring element, the second primary body comprising a second joint surface configured to cooperate with the prosthetic or natural bone head and a second bearing surface configured for placement against the patient's shoulder blade socket, the second anchoring element extending from the second bearing surface; wherein a difference between a radius of curvature of the first bearing surface and a radius of curvature of the second bearing surface is at least 4 mm.

2. The set of claim 1, wherein both the first and second bearing surfaces comprise convex curved surfaces.

3. The set of claim 1, wherein both the first and second joint surfaces comprise concave curved surfaces.

4. The set of claim 1, wherein both the first and second bearing surfaces comprise smooth surfaces.

5. The set of claim 1, wherein the first anchoring element and the second anchoring element are keels.

6. The set of claim 1, wherein the first and second glenoid components are of a first size, the set further comprising:
a third glenoid component comprising a third joint surface and a third bearing surface; and
a fourth glenoid component comprising a fourth joint surface and a fourth bearing surface, wherein
each of the third and fourth joint surfaces is configured to cooperate with the prosthetic or natural humeral head, and
each of the third and fourth bearing surfaces is configured for placement against the shoulder blade socket of the shoulder joint,
the third and fourth glenoid components are of a second size larger than the first size,
a radius of curvature of the third joint surface is the same as a radius of curvature of the fourth joint surface,
a radius of curvature of the third bearing surface is different than a radius of curvature of the fourth bearing surface.

7. The set of claim 6, wherein a radius of curvature of the first bearing surface is the same as a radius of curvature of the third bearing surface.

8. The set of claim 7, wherein a radius of curvature of the second bearing surface is the same as a radius of curvature of the fourth bearing surface.

9. The set of claim 6, wherein the radius of curvature of each of the third and fourth joint surfaces is greater than the radius of curvature of each of the first and second joint surfaces.

10. The set of claim 6, wherein the joint surfaces of the third and fourth glenoid components have an increased edge-to-edge expanse compared to the joint surfaces of the first and second glenoid components.

11. The set of claim 6, further comprising:
a fifth glenoid component comprising a fifth joint surface and a fifth bearing surface; and
a sixth glenoid component comprising a sixth joint surface and a sixth bearing surface, wherein
each of the fifth and sixth joint surfaces is configured to cooperate with the prosthetic or natural humeral head,
each of the fifth and sixth bearing surfaces is configured for placement against the shoulder blade socket of the shoulder joint,
the fifth and sixth glenoid components are of a third size larger than the second size,
a radius of curvature of the fifth joint surface is the same as a radius of curvature of the sixth joint surface, and
a radius of curvature of the fifth bearing surface is different than a radius of curvature of the sixth bearing surface.

12. The set of claim 11, wherein a radius of curvature of each of the fifth and sixth joint surfaces is greater than the radius of curvature of each of the third and fourth joint surfaces.

13. The set of claim 11, wherein the joint surfaces of the fifth and sixth glenoid components have an increased edge-to-edge expanse compared to the joint surfaces of the third and fourth glenoid components.

14. The set of claim 11, wherein a radius of curvature of the fifth bearing surface is greater than the radius of curvature of the third bearing surface but smaller than the radius of curvature of the fourth bearing surface.

15. The set of claim 14, wherein a radius of curvature of the sixth bearing surface is greater than the radius of curvature of the third bearing surface and the fourth bearing surface.

16. The set of claim 1, wherein the difference between the radius of curvature of the first bearing surface and the radius of curvature of the second bearing surface is at least 8 mm.

* * * * *